(12) United States Patent
Centeno et al.

(10) Patent No.: US 10,905,721 B2
(45) Date of Patent: Feb. 2, 2021

(54) DEVICE AND METHODS FOR PLATELET LYSIS OR ACTIVATION

(71) Applicant: Regenerative Sciences, LLC, Broomfield, CO (US)

(72) Inventors: Christopher J. Centeno, Broomfield, CO (US); Neven Steinmetz, Broomfield, CO (US); Ian Stemper, Broomfield, CO (US); Dustin Berger, Broomfield, CO (US)

(73) Assignee: REGENEXX, LLC., Des Moines, IA (US)

( * ) Notice: Subject to any disclaimer, the term of this patent is extended or adjusted under 35 U.S.C. 154(b) by 403 days.

(21) Appl. No.: 15/852,309

(22) Filed: Dec. 22, 2017

(65) Prior Publication Data

US 2018/0117086 A1 May 3, 2018

Related U.S. Application Data

(63) Continuation-in-part of application No. 14/761,828, filed as application No. PCT/US2014/013351 on Jan. 28, 2014, now abandoned.
(Continued)

(51) Int. Cl.
*A61K 35/19* (2015.01)
*C12N 5/078* (2010.01)
(Continued)

(52) U.S. Cl.
CPC .............. *A61K 35/19* (2013.01); *A61K 45/06* (2013.01); *C12M 47/06* (2013.01);
(Continued)

(58) Field of Classification Search
CPC ................ C12N 5/0018; C12N 5/0644; C12N 2523/00; A61K 35/19; A61K 45/06;
(Continued)

(56) References Cited

U.S. PATENT DOCUMENTS

| 4,327,799 A | 5/1982 | Scheiwe et al. |
| 5,834,418 A | 11/1998 | Brazeau et al. |

(Continued)

FOREIGN PATENT DOCUMENTS

| EP | 1007061 B1 | 6/2000 |
| WO | WO-2006-137778 | 12/2006 |
| WO | WO 2008-035240 | 3/2008 |

OTHER PUBLICATIONS

International Preliminary Report on Patentability on International Application No. PCT/US2017/068141 dated Jun. 25, 2019, 8 pages.
(Continued)

*Primary Examiner* — Gautam Prakash
(74) *Attorney, Agent, or Firm* — Adsero IP

(57) ABSTRACT

Apparatus, kit and method embodiments are disclosed herein that provide for the production of a modified autologous platelet mixture at a patient bedside for contemporaneous reinjection to the patient using a platelet lysis apparatus. Representative platelet lysis apparatus include a sample tube and a compressed gas source connected to or near the sample tube. The compressed gas source provides for the release of expanding gas into direct or indirect contact with an exterior surface of the sample tube to freeze a platelet containing mixture within the sample tube. An optional housing supports the sample tube and compressed gas source in an operative relationship with each other.

17 Claims, 11 Drawing Sheets

Related U.S. Application Data

(60) Provisional application No. 61/824,090, filed on May 16, 2013, provisional application No. 61/849,444, filed on Jan. 28, 2013, provisional application No. 62/437,828, filed on Dec. 22, 2016.

(51) Int. Cl.
| | |
|---|---|
| *C12M 1/00* | (2006.01) |
| *A61K 45/06* | (2006.01) |
| *C12N 5/00* | (2006.01) |
| *G01N 33/86* | (2006.01) |
| *C12M 1/42* | (2006.01) |

(52) U.S. Cl.
CPC ......... *C12N 5/0018* (2013.01); *C12N 5/0644* (2013.01); *C12M 35/04* (2013.01); *C12N 2523/00* (2013.01); *G01N 33/86* (2013.01)

(58) Field of Classification Search
CPC ....... C12M 47/06; C12M 35/04; G01N 33/86; G01N 33/5005; A01N 1/0268; A01N 1/0263; B01L 3/502715; B01L 2300/0672; B01L 2300/0887; B01L 2200/027; B01L 2400/0481; B01L 2400/0694; B01L 2400/086; B01L 2300/047; B01L 7/50; B01L 2400/0677; B01L 2400/0406; B01L 2300/0816; B01L 2400/0683; B01L 2300/044
See application file for complete search history.

(56) References Cited

U.S. PATENT DOCUMENTS

| | | | |
|---|---|---|---|
| 5,935,848 A * | 8/1999 | Sputtek et al. | A01N 1/02 435/307.1 |
| 7,861,540 B2 * | 1/2011 | Cloutier et al. | G01N 1/42 62/63 |
| 8,037,696 B2 | 10/2011 | Shaham et al. | |
| 2002/0187547 A1 | 12/2002 | Taylor et al. | |
| 2011/0280952 A1 | 11/2011 | Caramella et al. | |
| 2014/0127314 A1 | 5/2014 | Copland et al. | |
| 2016/0002598 A1 | 1/2016 | Centeno et al. | |

OTHER PUBLICATIONS

Curasan AG: Patent granted for platelet-mediator concentrate, Aug. 30, 2012, 2 pages.

Schmolz et al., An Innovative, Centrifugation-free Method to Prepare Human Platelet Mediator Concentrates Showing Activities Comparable to Platelet-rich Plasma, Jun. 2011, 13 pages.

Curasan AG: Scouts for Sales Partners for ATR, Press Release, Jul. 2010, 2 pages.

International Search & Written Opinion dated Apr. 16, 2018, 16 pages.

Extended European Search Report, International Application No. PCT-US2917/068141, dated Jun. 25, 2020, 9 pages.

* cited by examiner

DEVICE AND METHODS FOR PLATELET LYSIS OR ACTIVATION

RELATED APPLICATIONS

This application is a non-provisional application of U.S. provisional application No. 62/437,828, entitled "Device and Methods for Platelet Lysis or Activation", filed on Dec. 22, 2016; and a Continuation-in-part of U.S. application Ser. No. 14/761,828, entitled "Device and Methods for Platelet Lysis or Activation", and filed Jul. 17, 2015; which is a 371 of International application number PCT/US14/13351 entitled "Device and Methods for Platelet Lysis or Activation", and filed on Jan. 28, 2014; which claims the benefit of U.S. provisional application No. 61/824,090, entitled "Device and Methods for Platelet Lysis", and filed on May 16, 2013; and claims the benefit of U.S. provisional application No. 61/849,444, entitled "Platelet Lysate Machine", filed on Jan. 28, 2013. Each of these references is incorporated herein by reference in its entirety.

TECHNICAL FIELD

The embodiments disclosed herein are directed toward apparatus, system, kit and methods for platelet lysis and/or activation. Embodiments are more particularly directed toward systems and methods for platelet lysis and/or activation which may be implemented at a patient's bedside during a single treatment session.

BACKGROUND

Platelets are small, disc-shaped, non-nucleated cell fragments which circulate in the blood of mammals. Platelets are a natural source of growth factors including but not limited to platelet-derived growth factor (PDGF), transforming growth factor beta (TGF-β), fibroblast growth factor (FGF), insulin-like growth factor (IGF), epidermal growth factor (EGF), vascular endothelial growth factor (VEGF) and others. These growth factors are released from a granules within the platelets. The platelets also include δ, γ and λ-granules, cytokines, proteins, cellular components, mRNA, ribosomal RNA, transfer RNA, DNA, and other small molecules including chemicals, hormones and signaling molecules. These factors and other platelet contents are referred to herein collectively as "therapeutic platelet contents." Therapeutic platelet contents have been shown to play a significant role in the repair and regeneration of injured or damaged biological tissue including but not limited to human connective tissues. Local application of various platelet-derived therapeutic platelet contents in increased concentration by the administration of a mixture enriched with the content of autologous platelets is a known technique to promote ligament, tendon, muscle, and cartilage repair, and tissue healing.

Many methods are known to cause or induce lysis or the disruption of a cellular or cell fragment membrane for the purpose of releasing the contents of the cell or cell fragment (including platelets) into solution. Typical methods may be grouped into six categories: optical, mechanical, acoustic, electrical, chemical and thermal. One or more of the foregoing methods can be employed for batch lysis of a platelet containing mixture. Alternatively, lysis methods have been applied to a single cell for analysis of its contents.

Known methods of platelet lysis require extensive capital equipment, specialized disposable consumables, trained personnel and complex techniques. Additionally, the time required to create modified platelet mixture using known techniques may be sufficiently lengthy that it is not reasonable to begin with freshly drawn or pre-processed patient blood or bone marrow and create an injectable modified platelet mixture within the time frame of a single office visit. Furthermore, a medical provider is very unlikely to have access to a clean room and laboratory equipment necessary to produce and process a suitable modified platelet mixture on-site. These difficulties have restricted the adoption of autologous platelet lysate therapies to specialized labs, at high cost, and prohibited the use of autologous platelet lysate therapies in a typical clinical setting. The embodiments disclosed herein are directed toward overcoming one or more of the problems discussed above.

SUMMARY OF THE EMBODIMENTS

Apparatus, system, kit and method embodiments are disclosed herein that provide for the production of a modified autologous platelet mixture at a patient's bedside for contemporaneous reinjection to the patient. In certain embodiments, all of the steps including but not limited to blood or bone marrow draw, platelet lysis and/or platelet activation, mixture preparation and reinjection to a patient are accomplished in a single office or clinic visit without necessarily relocating the patient. Method embodiments include the preparation of a modified mixture from a platelet containing mixture utilizing one or more platelet lysis apparatus, system, kit and method embodiments as disclosed herein.

Certain embodiments include a platelet lysis apparatus. A representative platelet lysis apparatus includes a sample tube and a compressed gas source connected to or near the sample tube. The compressed gas source provides for the release of expanding gas into direct or indirect contact with an exterior surface of the sample tube to freeze a platelet containing mixture within the sample tube. An optional housing supports the sample tube and compressed gas source in an operative relationship with each other. For example, the housing, in certain embodiments, includes a threaded connection to mate with corresponding threads on the compressed gas source.

In embodiments having a housing, the housing typically defines a gas flow path from an outlet from the compressed gas source around or near an exterior surface of the sample tube. The platelet lysis apparatus may optionally include a gas release or gas control mechanism, for example a trigger, pushbutton, switch, valve or threaded release connection configured to control the rate, duration or quantity of gas released from the compressed gas source. The housing may include an insulated exterior surface. The housing may also, in certain embodiments, include retention structures to secure the sample tube and/or the compressed gas source to the housing.

In certain embodiments, the sample tube retention structure includes male or female threads defined by the exterior surface of the sample tube and corresponding male or female threads defined by an interior surface of the housing. In these embodiments, the threads defined by the exterior surface of the sample tube and the corresponding threads defined by the interior surface of the housing may optionally be configured to engage loosely as to define an interior spiral channel when the sample tube is threaded into the housing and thus to define a gas pathway between the exterior surface of the sample tube and the interior surface of the housing.

In certain embodiments, the sample tube is fabricated from a metallic material and therefore includes a metal surface, or is fabricated from a plastic having a high thermal conductivity, or is fabricated from a plastic with subsequent sputtering of a metal coating, or is otherwise fabricated to facilitate heat transfer between the platelet containing mixture and the expanding gas released from the compressed gas source.

Alternative embodiments of a platelet lysis apparatus optionally include a heat transfer casing in thermal contact with the sample tube. The heat transfer casing is positioned to be in direct or indirect contact with the expanding gas released from the compressed gas source. The heat transfer casing may be supported by the housing such that the housing defines a gas flow path from the compressed gas source around an exterior and/or an interior surface of the heat transfer casing. In certain embodiments, the heat transfer casing includes at least one opening providing for direct contact between the gas released from the compressed gas source and the exterior surface of the sample tube.

Other alternative embodiments of a platelet lysis apparatus optionally include a chilled thermal mass element placed in thermal contact with the sample tube. Typically, the chilled thermal mass element is either a solid material or a liquid filled container defining an opening to receive the sample tube. In either configuration, the chilled thermal mass element preferably has significant thermal mass. In use, the chilled thermal mass element is chilled to a temperature below an ambient temperature prior to the placement of the sample tube into thermal contact with the chilled thermal mass element. Then, expanding gas from the compressed gas source may be directly or indirectly contacted with the chilled thermal mass element and/or the heat transfer casing and/or the sample tube to freeze some or all of the platelet containing mixture within the sample tube and cause platelet lysis.

Embodiments disclosed herein can include any combination of sample tubes, housings, heat transfer casings, compressed gas sources and chilled thermal mass elements. Each of these embodiments may define retention structures to hold adjacent structures in a proper operative configuration and also to define one or more gas flow paths. For example, retention structures between adjacent structures can include male or female threads defined by an exterior surface of one structure and corresponding male or female threads defined by an interior surface of the adjacent structure. The threads defined by the exterior surface and the corresponding threads defined by the adjacent interior surface may be configured to engage loosely as to define an interior spiral channel when the adjacent structures are threaded together and thus define a gas pathway between the exterior surface and the interior surface.

Method embodiments disclosed herein can include the steps of obtaining a platelet containing mixture from a patient. Preliminary processing steps may be performed to concentrate platelets in the initial platelet containing mixture, for example blood or bone marrow, into a more concentrated platelet containing mixture. A quantity of the platelets within the platelet containing mixture is then frozen to induce platelet lysis and/or activation utilizing any embodiment of platelet lysis apparatus described herein. Method embodiments may optionally further comprise reinjection of the modified mixture containing the contents of lysed platelets into the patient.

Kit embodiments include any embodiment of platelet lysis apparatus disclosed herein and ancillary equipment and materials. The ancillary equipment and materials may include but are not limited to syringes, needles, processing tubes, tube closures such as caps or septa, freezing apparatuses such as a compressor based refrigeration unit or freezer unit, ice and similar chilled materials, tube racks, centrifuges, gloves, pipettes, method instructions, cases or other apparatuses.

DETAILED DESCRIPTION

Figure 1:
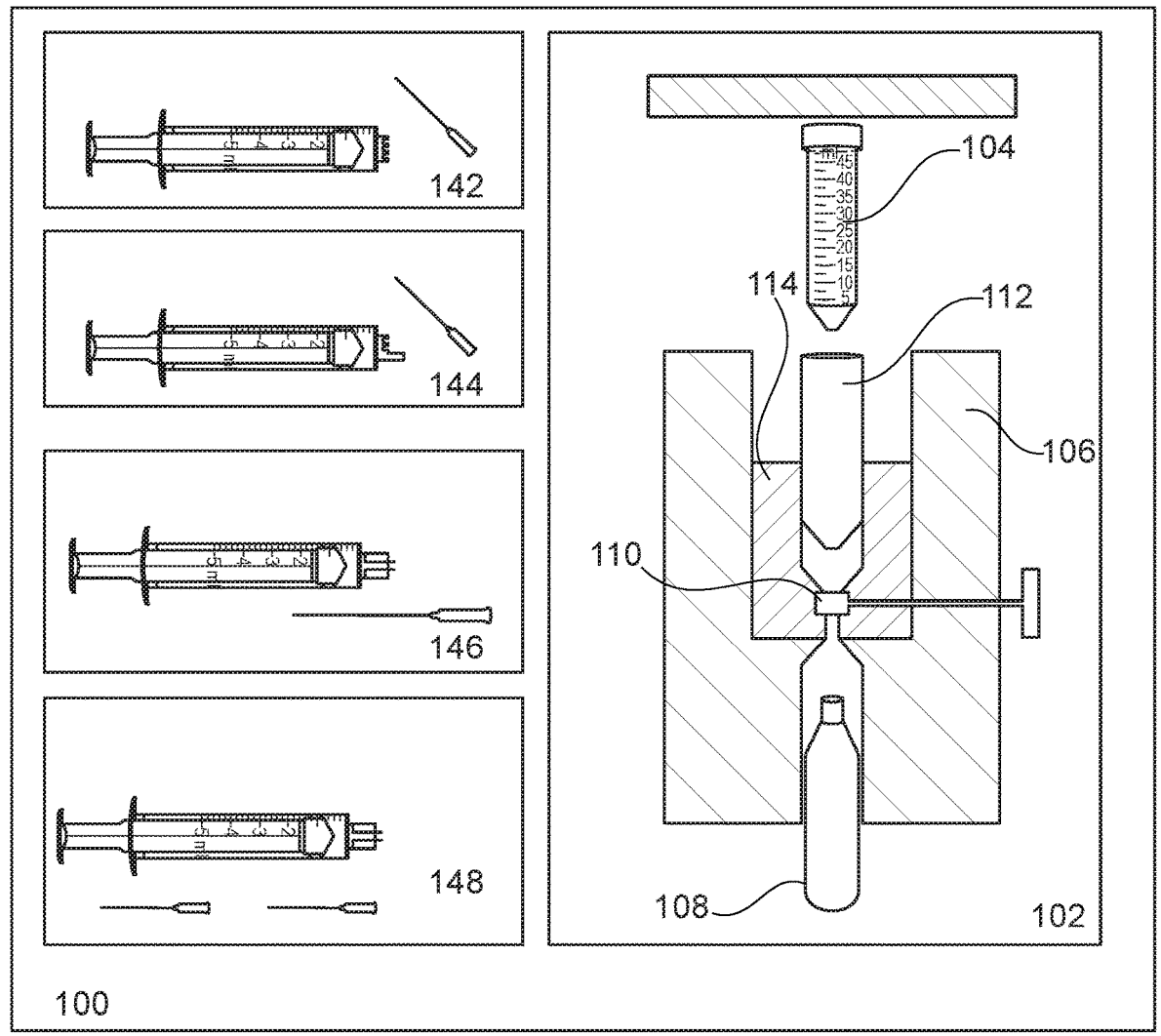
FIG. 1 is a schematic diagram of a platelet lysis kit as disclosed herein.
Figure 1:
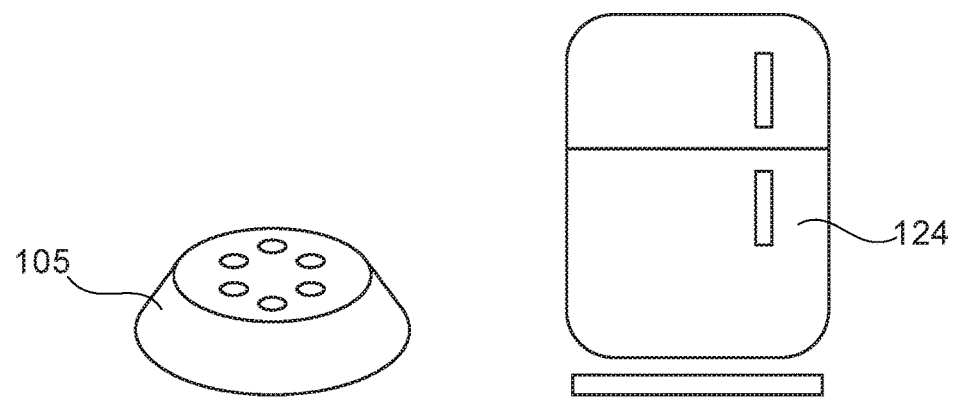

Unless otherwise indicated, all numbers expressing quantities of ingredients, dimensions, reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element," "structure," or "component" encompass elements, structures, and components comprising one unit and elements, structures and components that comprise more than one unit unless specifically stated otherwise.

In this application and the claims, any reference to blood, bone marrow, plasma, other blood derivatives including plasma, or other bodily fluids is not limiting and in all cases can include reference to any of blood, bone marrow, other blood derivatives including plasma, or other bodily fluids.

The various apparatus, system, kit and method embodiments disclosed herein provide for the production of a modified autologous platelet mixture at a patient bedside for contemporaneous reinjection to the patient. In certain embodiments, all of the steps including but not limited to blood, bone marrow or other fluid draw, platelet lysis and/or platelet activation, mixture preparation and reinjection to a patient may be accomplished in a single office or clinic visit without relocating the patient. In alternative embodiments, a portion or all of the platelets may be obtained from pooled allogeneic platelet containing plasma. Additional embodiments of apparatus, system, kit and methods for platelet lysis and/or activation are disclosed in co-owned U.S. patent application Ser. No. 14/761,828, publication number 2016-

0002598, the disclosure of which is incorporated herein by reference for all matters disclosed therein.

The phrase "platelet lysis" is defined herein as a process or method that results in the rupture of a platelet cell membrane, thereby releasing therapeutic platelet contents from the platelet. The phrase "platelet activation" is defined herein as a process that triggers a series of events that control platelet aggregation, adherence and the release of specific proteins and growth factors to promote ligament, tendon, muscle, and cartilage repair, and tissue healing. Platelet activation can occur in the blood stream, for example in response to a wound. The platelet activation referred to herein occurs outside of the human body and causes the release of therapeutic platelet contents from a platelet without necessarily causing the rupture of a platelet cell membrane.

Accordingly, the embodiments herein generally include an apparatus, system, kit and methods which is configured to accept a platelet containing mixture, induce lysis and/or activation of one or more platelet bodies within the platelet containing mixture and provide the resulting modified platelet mixture in a manner suitable for reinjection to the patient. The described embodiments therefore provide for the creation of an injectable modified platelet mixture without the requirement of additional laboratory equipment, aside from the equipment and associated materials described herein.

In various apparatus, system, kit and method embodiments, a modified platelet mixture is created by freezing a platelet containing mixture thereby causing some or all of the platelet bodies to release their therapeutic platelet contents through lysis and/or activation. For example, FIG. 1, which schematically illustrates a kit embodiment 100 that features the use of a platelet lysis apparatus 102 to freeze some or all of a platelet containing mixture or concentrated platelet pellet (collectively referred to herein as "platelets") to induce lysis and/or activation of a quantity of the platelets. In the FIG. 1 kit embodiment 100, a processing tube 104 is prepared to contain a patient's autologous platelets. Typically, the patient's autologous platelets are derived from the patient's blood and/or bone marrow. In alternative embodiments, a portion or all of the platelets may be obtained from pooled allogeneic platelet containing plasma. As noted above, the platelets may have been pre-processed to form a concentrated platelet pellet. Alternatively, the platelets may be diluted, mixed with fluids or otherwise modified. In certain embodiments, the platelets will be pre-processed and prepared from blood or bone marrow drawn from the patient at the commencement of a treatment session. Alternatively, the platelets may be prepared from blood or bone marrow drawn from the patient at an earlier date and stored before or after pre-processing.

More specifically, in certain embodiments, blood, bone marrow, plasma or another bodily fluid is extracted from a patient using a conventional extraction technique. The drawn fluid could then be subjected to a centrifuge step in centrifuge 105 to separate various fluid components. Additional processing can include the addition of anticoagulants or other materials to the drawn blood, bone marrow or fluid. Blood components such as red blood cells can be withdrawn according to conventional techniques leaving behind a concentrated platelet mixture or pellet. Alternatively, the concentrated platelet mixture can be withdrawn and transferred to another sample tube for further processing. The centrifuge 105 shown on FIG. 1 will typically be equipment provided by a technician and is therefore not part of kit 100, however, in alternative embodiments, a centrifuge or other concentrating apparatus may be included with the kit 100.

All fluid or biological material transfers will be made in a manner to maintain sterility. In the above example, the blood or bone marrow may be processed with a centrifuge 105, followed by extraction of red blood cells and/or platelet-poor plasma through a septum cap or other sterile barrier sealing the processing tube 104 or another processing vessel. Additional processing steps may be performed to further concentrate the platelets in the original processing tube 104 and/or one or more subsequent processing tubes.

After the initial preparation of the platelets, subsequent steps may be taken utilizing the platelet lysis apparatus 102 to cause lysis and/or activation of at least a portion of the platelets. The platelet lysis apparatus 102 may include some or all of the following components: processing tube 104, an apparatus housing 106, a compressed gas source 108 and a valve 110 or other gas release mechanism associated with the compressed gas source 108. In addition, in certain embodiments, the platelet lysis apparatus 102 may include a heat transfer casing 112 and/or a chilled thermal mass element 114, and/or various syringes and needles. The structure, function and use of each of these elements are described in detail below.

Figure 2:
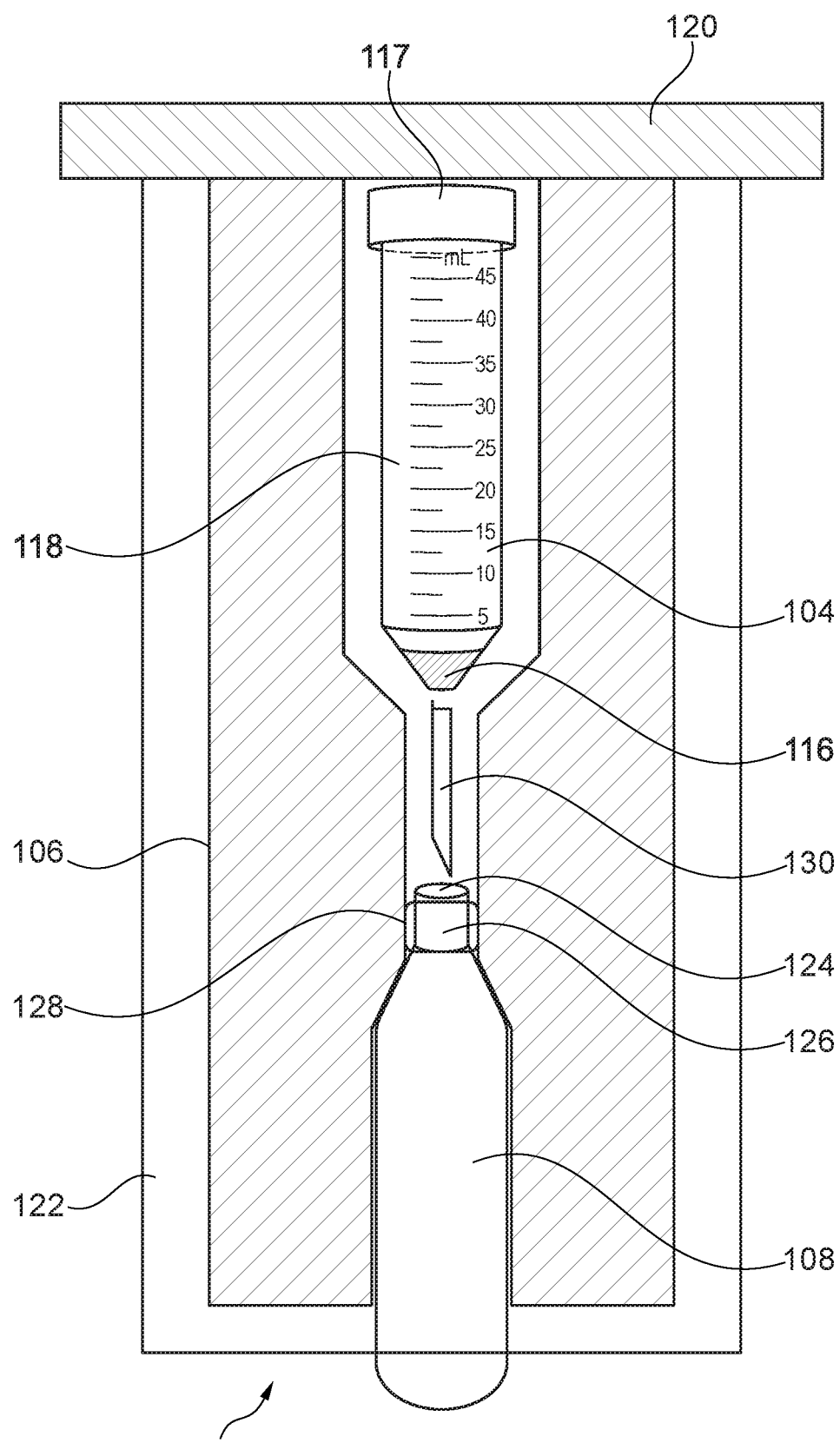
FIG. 2 is a schematic cross sectional diagram of a first embodiment of a platelet lysis apparatus as described herein.

FIG. 2 is a schematic cross-sectional view of one embodiment of platelet lysis apparatus 102 suitable for use with the kit 100 of FIG. 1. The FIG. 2 embodiment includes a processing tube 104 that, in use, would hold platelets, for example a platelet pellet 116, a platelet bearing fluid or other mixture containing platelets. The processing tube 104 is sealed with a cap 117, septum or other sterile barrier. The processing tube 104 is supported for lysis steps by a housing 106. The processing tube 104 is supported by the housing 106 in a position where expanding gas released from the compressed gas source 108 can directly or indirectly contact an exterior surface 118 of the processing tube 104 causing a rapid decrease in the temperature of the platelet pellet 116 or platelet bearing mixture and therefore cause rapid freezing of the same. As used herein, expanding gas released from the compressed gas source 108 is in "direct contact" with an exterior surface 118 of the processing tube 104 if the expanding gas physically contacts the exterior surface 118. The expanding gas released from the compressed gas source 108 is defined herein as being in "indirect contact" with the exterior surface 118 if the compressed gas physically makes contact with an intermediate device or structure that in turn is in thermal contact with the exterior surface 118. Various intermediate devices or structures which may be placed in thermal contact with the exterior surface 118 of the processing tube 104 are discussed in detail below. In certain embodiments, expanding gas is channeled into both direct and indirect contact with the exterior surface 118 of the processing tube 104.

In the FIG. 2 embodiment, one or more gaps, channels, openings or other gas flow pathways between the exterior surface 118 and an interior surface of the housing 106 provide for direct contact between expanding gas released from the compressed gas source 108 and the exterior surface 118 of the processing tube 104. Prior to release of compressed gas from the compressed gas source 108, both the processing tube 104 and the compressed gas source 108 must be secured by the housing 106 or secured to the housing 106. Therefore, the housing 106 serves to hold other elements in an operatively advantageous position while minimizing any physical or thermal risk to a technician using the platelet lysis apparatus 102. In particular, the housing 106 may include a secure lid 120, threads engaged with the compressed gas source 108 or processing tube 104, or other apparatus to secure the processing tube 104 and compressed gas source 108 to prevent physical expulsion of either of the processing tube 104 or compressed gas source 108 from the platelet lysis apparatus 102 when compressed gases are released. The housing 106 and/or secure lid 120 will typically also include venting structures positioned to safely vent expanding gas from the apparatus. The housing 106 and secure lid 120 may also include an insulated outer layer 122 which serves to prevent user contact with chilled or frozen internal structures. The housing 106 and/or insulated outer layer 122 may include ergonomic handles to help facilitate use and/or may include a platform or attachment structures that help provide stability to the platelet lysis apparatus 102.

As noted above, the platelet lysis apparatus 102 of FIG. 2 provides for direct contact between expanding gas released from the compressed gas source 108 and an exterior surface 118 of the processing tube 104. Although the compressed gas source is typically provided at room temperature, the expanding gas released therefrom is delivered at the exterior surface 118 having a dramatically reduced temperature, according to well-known thermodynamic principles. In particular, the expanding gas contacting the exterior surface 118 is delivered at a sufficiently reduced temperature to freeze some or all of the platelets in the processing tube 104. In certain embodiments, the exterior surface 118 or the entirety of the processing tube 104 is coated with or fabricated from a material, such as a metal, having a high level of thermal conductance.

The platelet lysis apparatus 102 may be implemented with compressed gas sources 108 of various sizes and configurations. The compressed gas source 108 may include a gas or gas blend of any suitable composition including but not limited to $CO_2$, $N_2$, $O_2$ and the like. The compressed gas source 108 may include compressed gas stored in a gas phase or a liquid phase. The compressed gas source 108 may be a single use cartridge or a larger canister meant to freeze multiple samples contained in multiple processing tubes 104 in unison, in succession, upon user demand, or to administer multiple freeze cycles to the same processing tube 104.

Figure 3A:
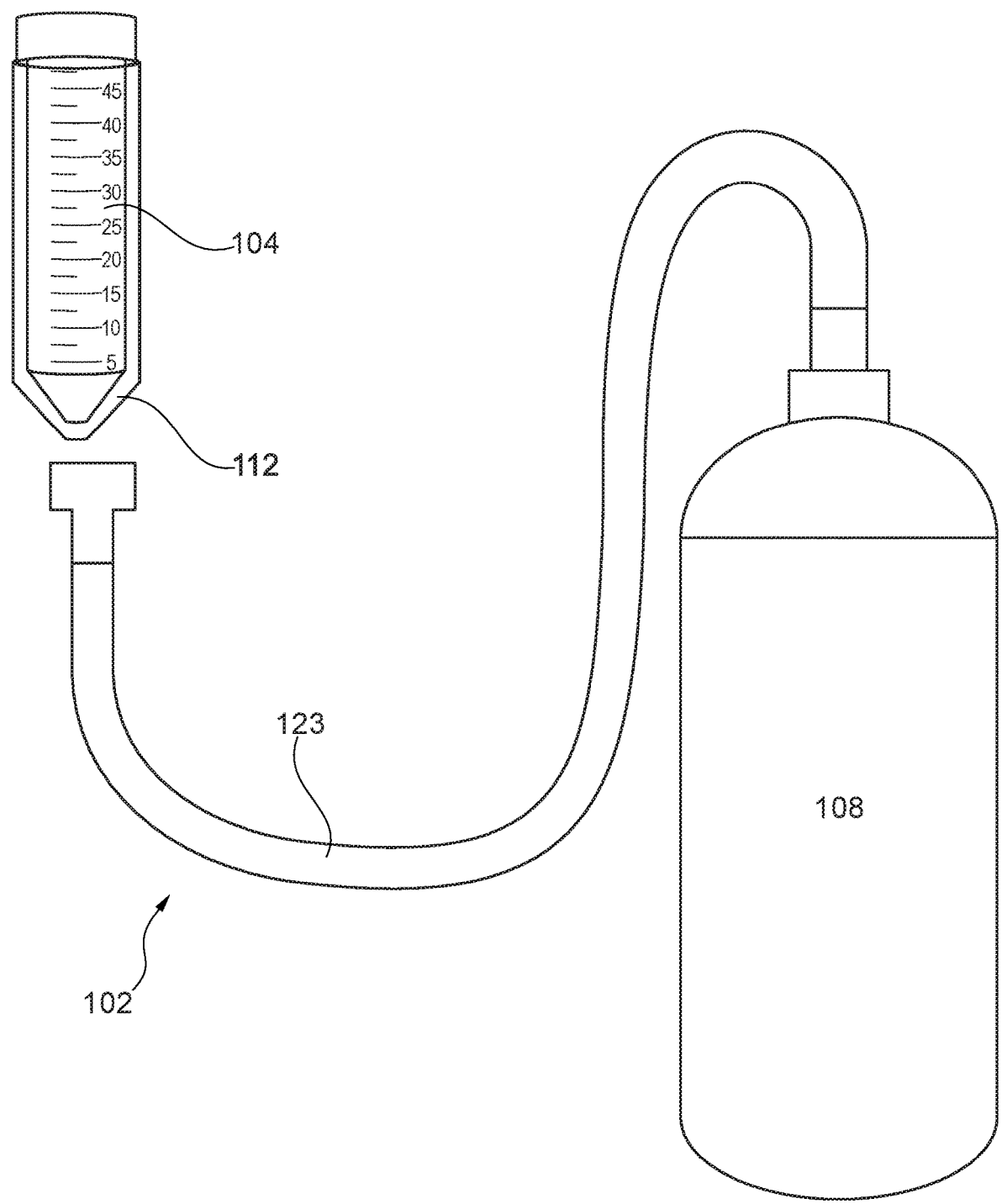
FIG. 3A is a schematic cross-sectional representation of an alternative platelet lysis apparatus embodiment.
Figure 3B:
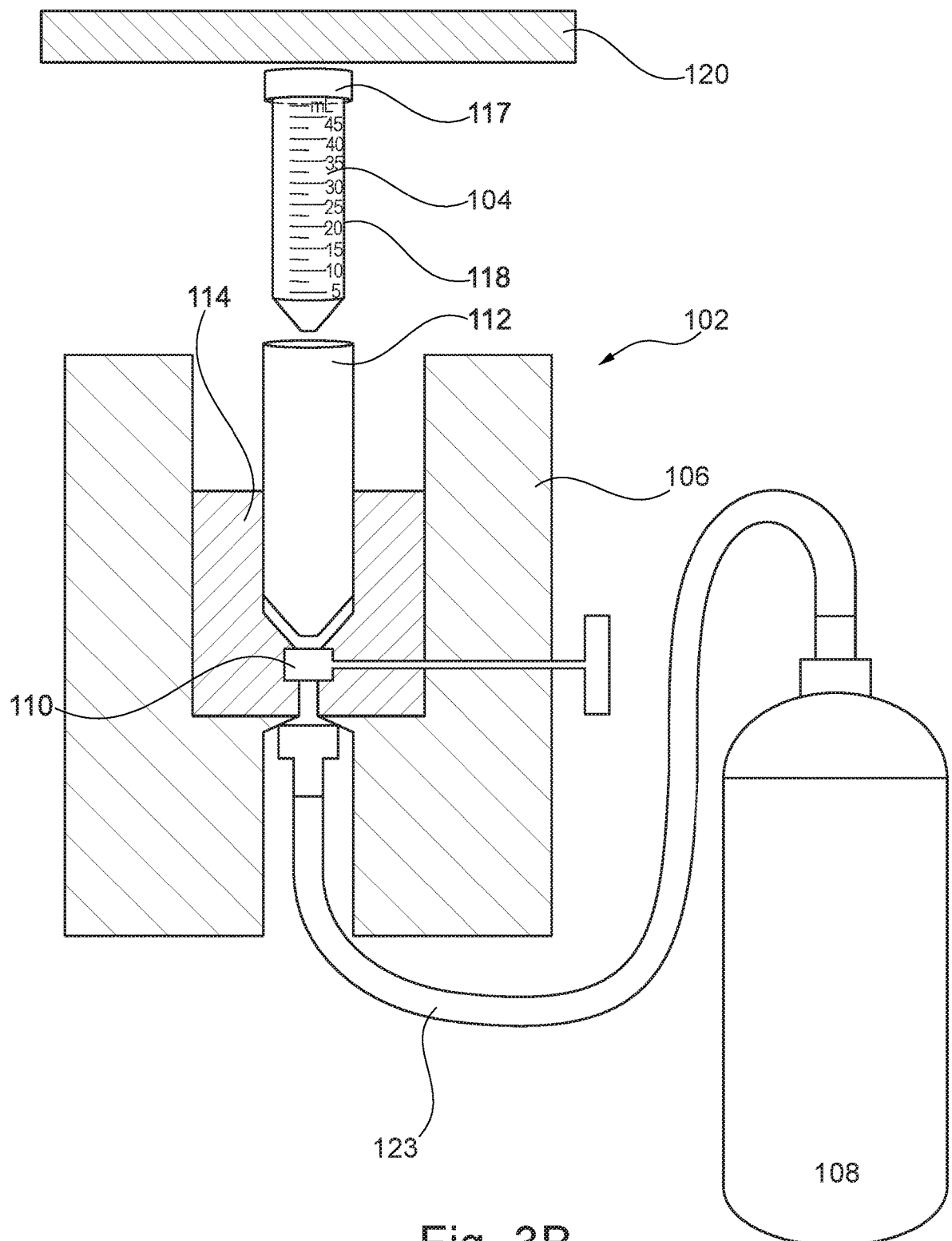
FIG. 3B is a schematic cross-sectional representation of an alternative platelet lysis apparatus embodiment.

Expanding gas may be delivered from the compressed gas source 108 to the processing tube 104 through a short connection or passageway as illustrated in FIG. 2, or through any desired combination of hoses, tubes, pipes or other suitable conduits. See for example the embodiments of FIG. 3A and FIG. 3B which include a larger volume compressed gas source 108 communicating with the housing 106 through a supply tube 123. Furthermore, the release of expanding gas from the compressed gas source 108 may be controlled with a valve or other apparatus of greater or lesser sophistication. For example, in a simple embodiment such as illustrated in FIG. 2, the compressed gas source 108 may be a single use cartridge having a metal seal 124 at a threaded end 126. The housing 106 may include a threaded coupling 128 sized to receive the threaded end 126 of the compressed gas source 108. In the simple embodiment of FIG. 2, a hollow needle or spike 130 associated with the housing 106 can be positioned to pierce the metal seal 124, thereby releasing gas from the compressed gas source 108 as the compressed gas source 108 is threaded into full contact with the housing 106. Alternatively, additional control over the release of gas may be provided with a valve 110, trigger, switch or other controlled gas release mechanisms, some of which are described in detail below.

A relatively more sophisticated gas release mechanism may be temperature control. For example, gas may be expelled in short bursts separated by pauses. This pattern may be programmed to continue until a specific temperature at the housing 106, processing tube 104 has been detected by a thermometer. Alternatively, the gas release mechanism may be controlled by a timed valve that permits gas to be released for a predetermined period of time after gas release commences.

As noted above, the housing 106 may define one or more gas flow paths around or near the exterior surface 118 of the processing tube 104 to facilitate heat exchange between the platelets or platelet bearing material within the processing tube 104 and the expanding gas from the compressed gas source 108, to promote freezing of the tube contents. For example, the housing 106 may define a gas flow path that is long and tortuous around the exterior surface 118 of the processing tube 104 to maximize gas contact with the exterior surface 118. Additional structures may be included in the platelet lysis apparatus 102 portion of the kit 100 to promote efficient freezing of the tube contents.

Figure 4:
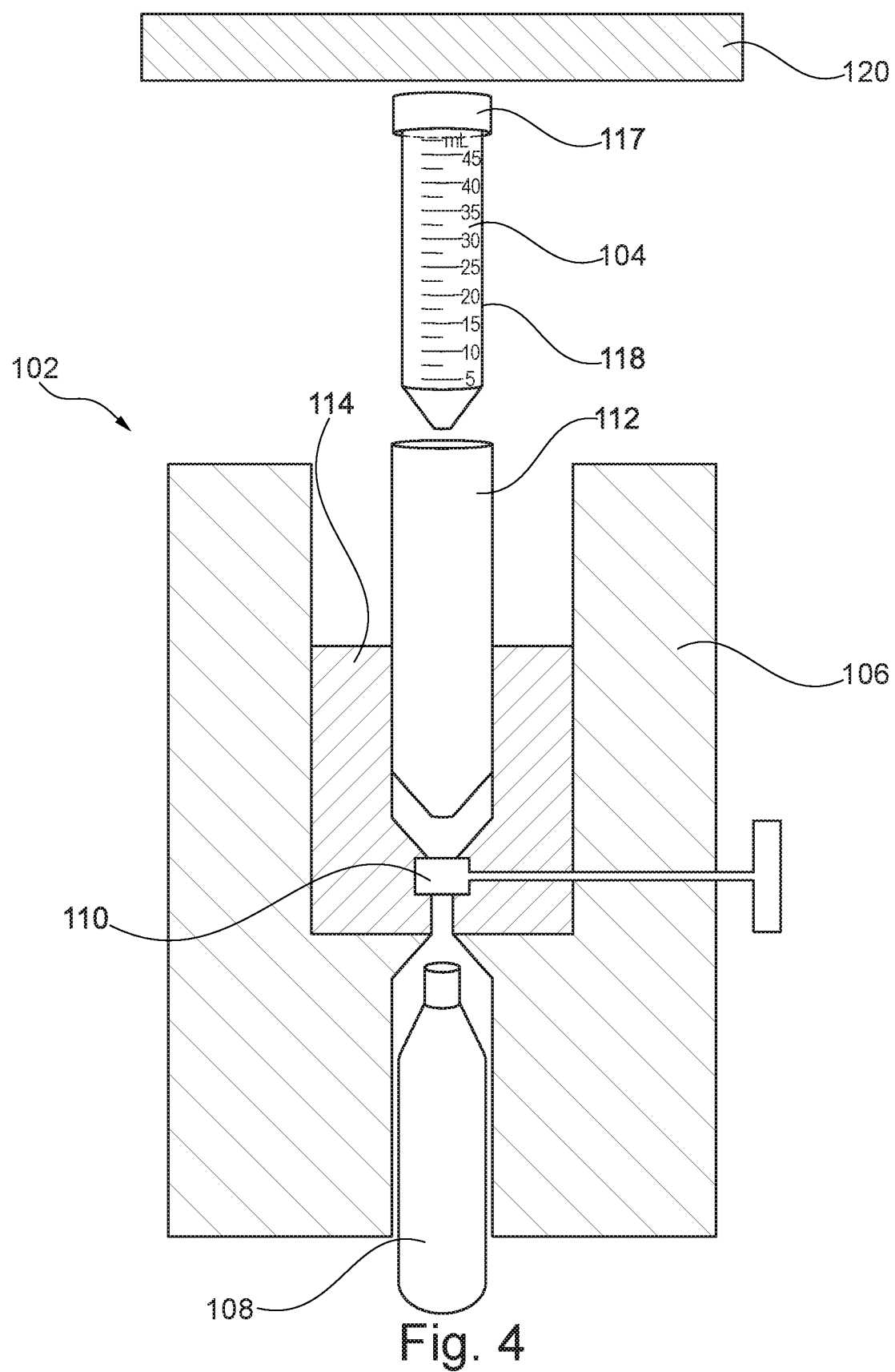
FIG. 4 is a schematic cross-sectional representation of another alternative platelet lysis apparatus embodiment.

As shown in FIG. 4, a kit 100 may include a heat transfer casing 112. The heat transfer casing 112 serves to promote thermal exchange between the contents of the processing tube 104 and the expanding gas released from the compressed gas source 108. The heat transfer casing 112 therefore is closely, but removably, associated with some or all of the exterior surface 118 of the processing tube 104. In one embodiment, the heat transfer casing 112 is a casing formed of a metal or other material having high thermal conductivity. The heat transfer casing 112 is shaped to closely surround all or a portion of the processing tube 104. Alternative heat transfer casing embodiments include but are not limited to a metal coil wrapped around the processing tube 104 or similar structures. In certain embodiments, the heat transfer casing 112 is placed in direct contact with the expanding gas and thermal energy is exchanged from the exterior surface 118 of the processing tube 104 indirectly to the expanding gas through the heat transfer casing 112. In other embodiments, the heat transfer casing 112 includes openings or perforations to allow direct contact between the expanding gas and an exterior surface 118 of the processing tube 104. The heat transfer casing 112 may be provided at room temperature, or may be chilled or frozen prior to use.

The freezing apparatus 102 may also include a chilled thermal mass element 114. The chilled thermal mass element 114 is chilled or frozen prior to use and thus serves, in conjunction with thermal transfer between the platelets and the expanding gas, to promote the effective freezing of the platelets contained within the processing tube 104. As illustrated in FIG. 4, the chilled thermal mass element 114 may be used in conjunction with a heat transfer casing 112. Alternatively, the platelet lysis apparatus 102 may include a chilled thermal mass element 114 but no heat transfer casing 112. When present, the chilled thermal mass element 114 may be implemented as a metal mass or mass of another material having suitably high thermal mass and thermal conductivity. For example, the thermal mass element 114 may be fabricated of metal, plastic, ceramic or another suitable material. Additionally, the thermal mass element 114 may be hollow or solid. Hollow embodiments may be filled with a liquid which is frozen or chilled, including but not limited to water or ethanol. A chilled thermal mass element 114 serves to both pre-cool the platelets within the processing tube 104 and promote thermal exchange between the contents of the processing tube 104 and expanding gas released from the compressed gas source 108. Both of these purposes serve to promote freezing and platelet lysis and/or activation.

Any embodiment of the chilled thermal mass element 114 will typically be chilled, cooled or frozen before use. Preliminary cooling of the chilled thermal mass element 114 may be accomplished by placing a non-cooled chilled thermal mass element 114 into a conventional compressor-based freezer 124 or refrigeration unit, placing the chilled thermal mass element 114 onto or into ice or another cooling medium, contacting the chilled thermal mass element 114 with chemical cooling packs, or by using known thermoelectric cooling, refrigeration or other cooling apparatus and methods. After the chilled thermal mass element 114 is suitably cool, it may be removed from the freezer 124 or other chilling mechanism and installed into the housing 106 of a platelet lysis apparatus 102 as generally illustrated in FIG. 4.

Figure 5:
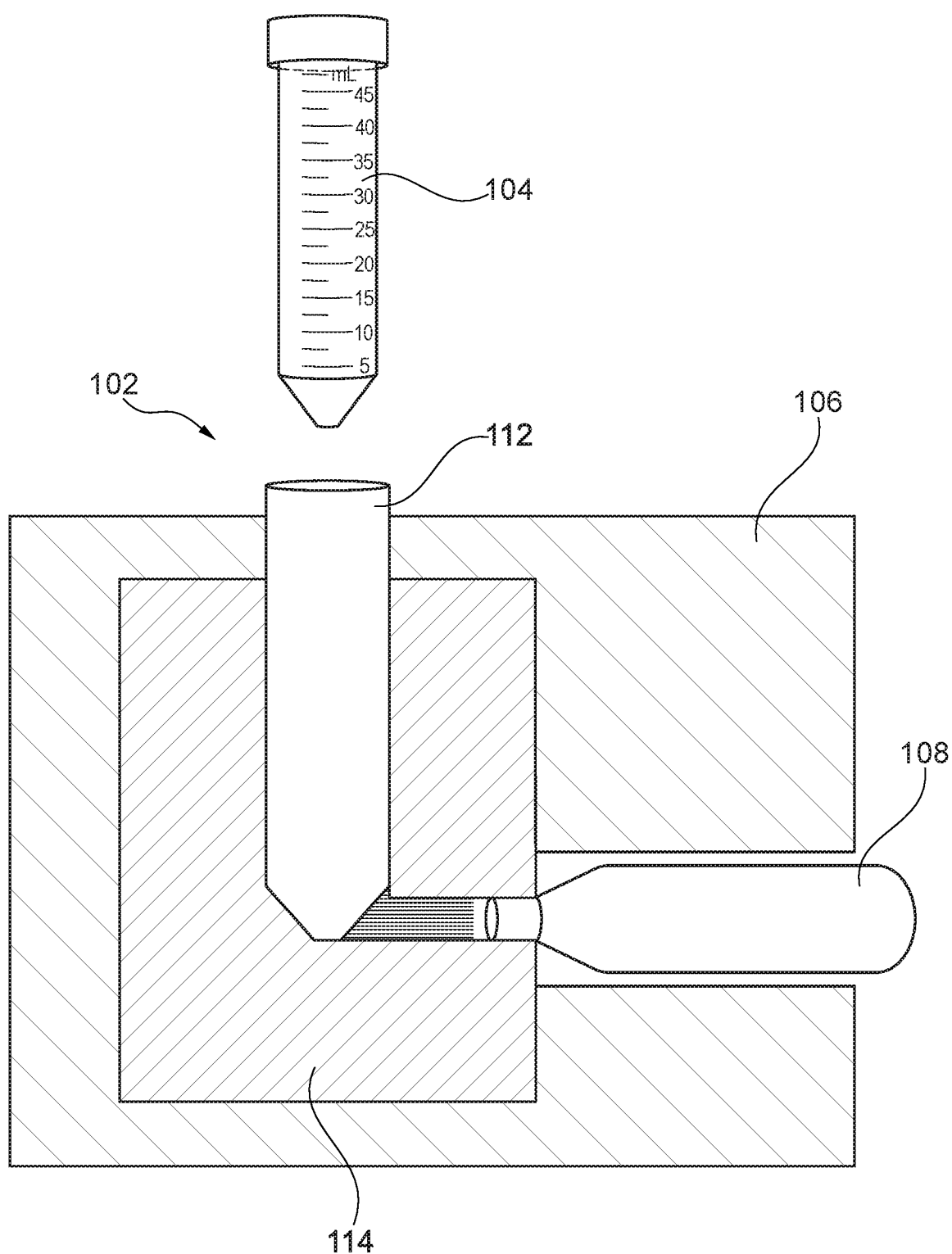
FIG. 5 is a schematic cross-sectional representation of another alternative platelet lysis apparatus embodiment.

The configuration illustrated in FIG. 4 is representative only and is not limiting upon the scope of the claimed embodiments. For example, the FIG. 4 embodiment shows a processing tube 104 coupled closely to a compressed gas source 108 within a housing 106 which holds these elements with substantially parallel centerlines. In the alternative embodiment of FIG. 5, the housing 106 supports the compressed gas source 108 at a right angle to the centerline of the processing tube 104, to enhance the contact time between the expanding gas released from the compressed gas source 108 perpendicular to the processing tube 104 centerline and the exterior surface 118. Alternative embodiments include configurations where the compressed gas source 108 is positioned at various angles relative to the centerline of the processing tube 104.

Figure 6:
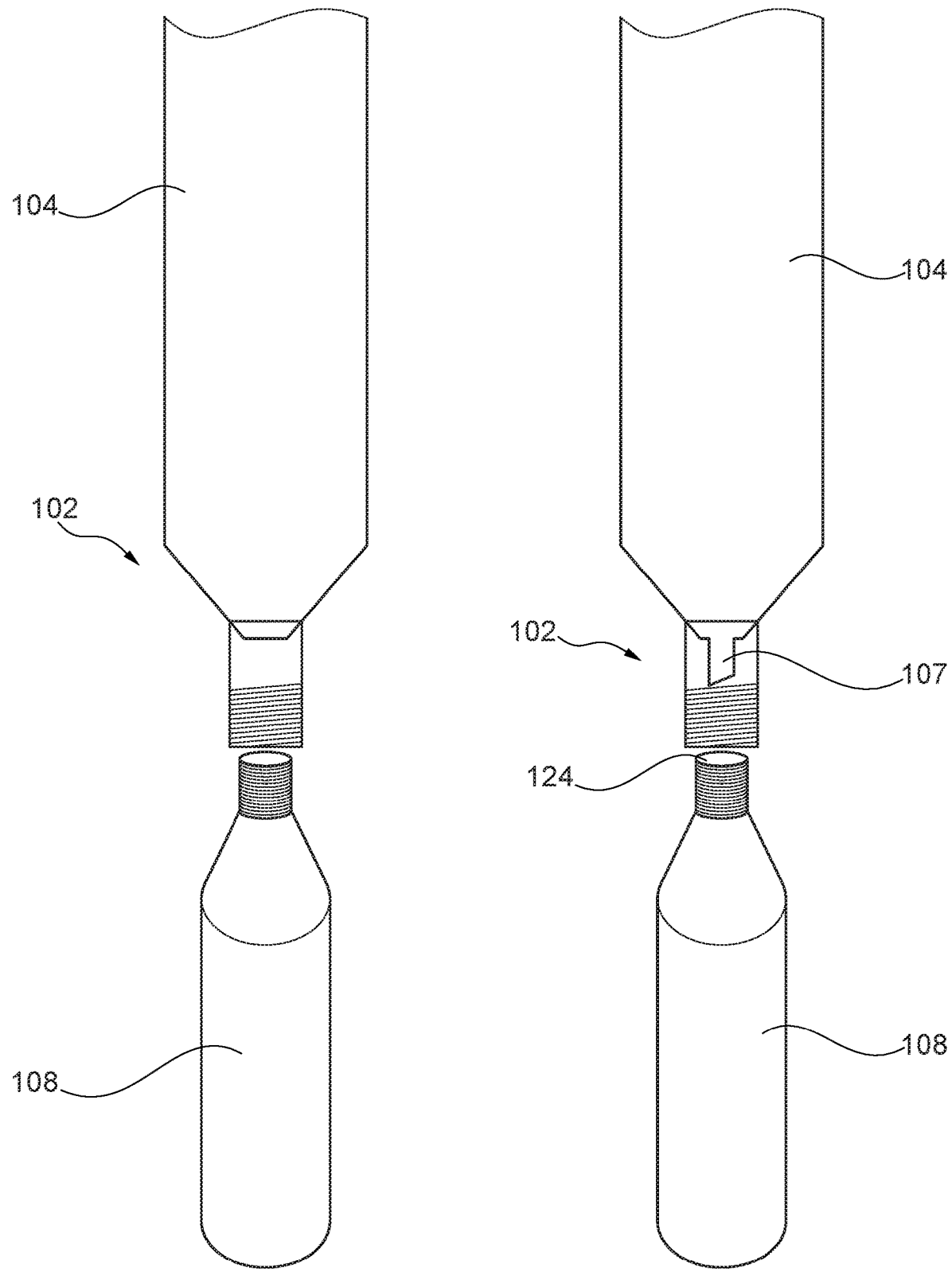
FIG. 6 is a schematic cross-sectional representation of another alternative platelet lysis apparatus embodiment.
Figure 7:
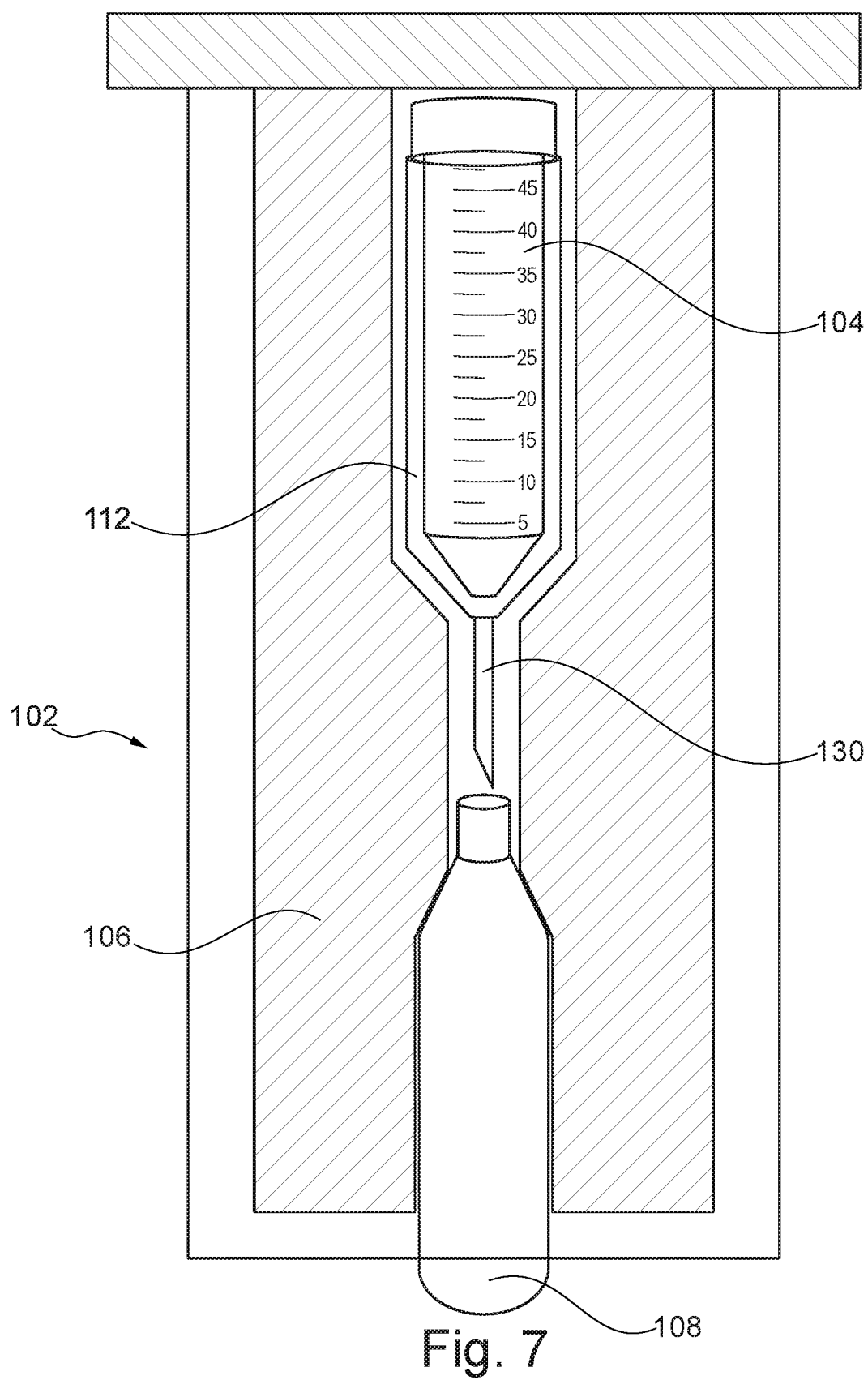
FIG. 7 is a schematic cross-sectional representation of another alternative platelet lysis apparatus embodiment.

As noted above, alternative embodiments of platelet lysis apparatus 102 may include any possible combination of housing 106, heat transfer casing 112, chilled thermal mass element 114, compressed gas source 108 and processing tube 104. For example, FIG. 6 schematically represents an embodiment where the compressed gas source 108 is coupled directly to a processing tube 104, which may include gas channels between double exterior walls. Thus, in the FIG. 6 embodiment there are no housing 106, heat transfer casing 112 or chilled thermal mass element 114 structures. In the FIG. 7 embodiment, no chilled thermal mass element 114 is required.

In each embodiment, expanding gas released from the compressed gas source 108 directly or indirectly cools the processing tube 104 causing the platelets contained therein to freeze. Accordingly, enhancements to the interface between the processing tube 104, housing 106, optional heat transfer casing 112 or optional chilled thermal mass 114 elements that promote thermal exchange between the contents of the processing tube 104 and the expanding gas can enhance the ability of the platelet lysis apparatus 102 to freeze platelets. Furthermore, as also noted above, user safety requires a secure interface between the platelet lysis apparatus 102 system elements so that expanding gas released from the compressed gas source 108 does not forcibly eject any system element. The goals of enhanced thermal exchange and enhanced user safety can be promoted by providing one or all of the housing 106, processing tube 104, heat transfer casing 112, compressed gas source 108 and/or chilled thermal mass element 114 with a secure connection to other system elements which may also serve to channel expanding gas in a desired manner.

Figure 8:
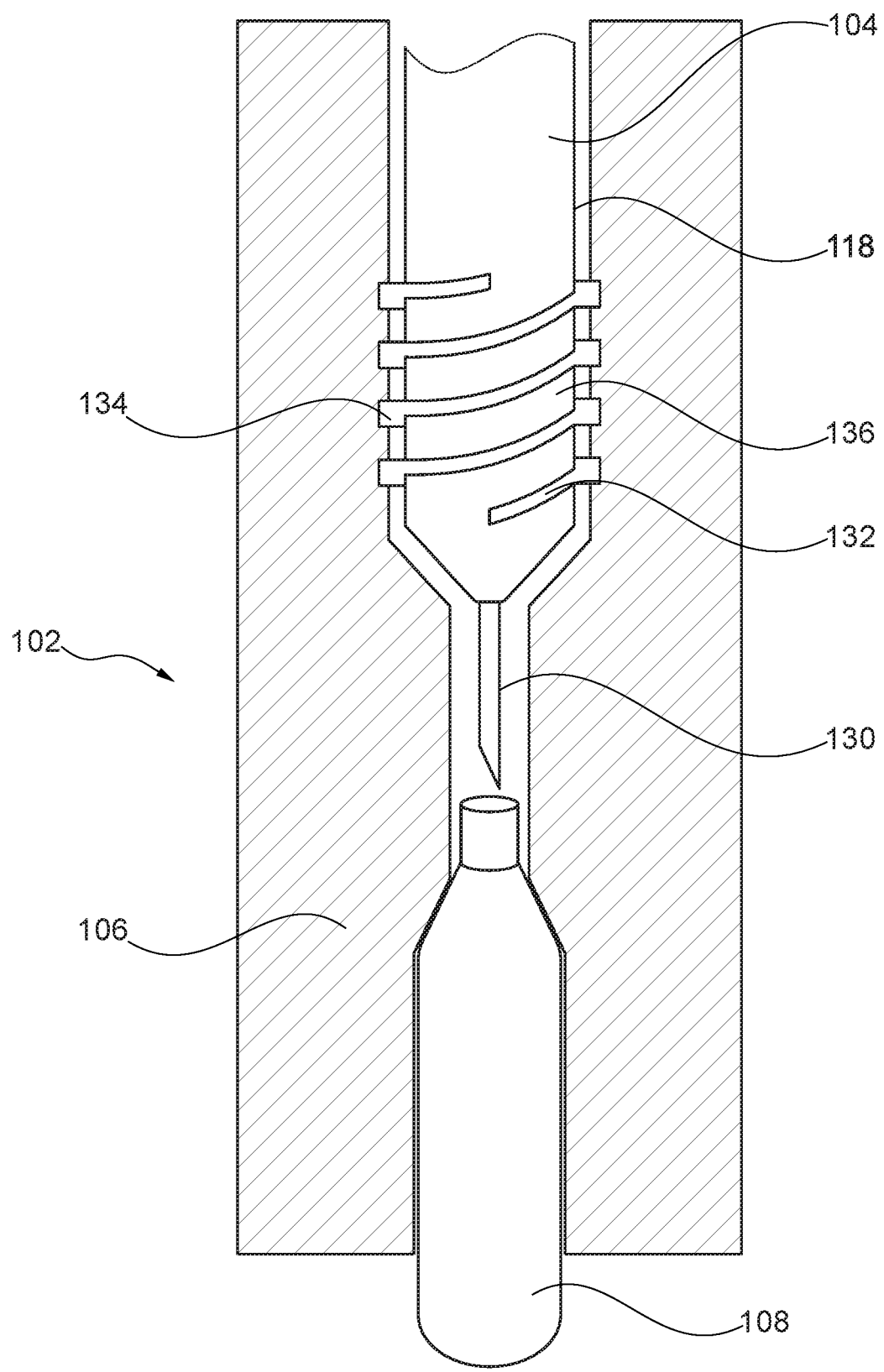
FIG. 8 is a schematic cross-sectional representation of another alternative platelet lysis apparatus embodiment.

For example, adjacent elements may be fitted with or formed into threaded structures which serve to secure elements together and also to channel gas flow. As shown in FIG. 8, the processing tube 104 may have an exterior surface 118 which defines one or more spiral male or female thread elements 132. In this embodiment, the housing 106 defines corresponding spiral male or female thread elements 134 which provide for a secure threaded interface between the processing tube 104 and the housing 106. Furthermore, the widely spaced structure of the threads 132 and 134 defines at least one gas flow channel 136 between threads that spirals around the exterior surface 118 of the processing tube 104. A similar gas flow channel can be accomplished with loosely fitting threads. Thus, expanding gas released from the compressed gas source 108 is channeled around the processing tube 104 and through the gas flow channel 136, enhancing both the contact time and contact area between the expanding gas and exterior surface 118 of the processing tube 104. The gas flow channel 136 may be made of a thermally insulating material so as to maximize heat transfer from the platelets to the expanding gas.

Although the embodiment shown in FIG. 8 shows a gas flow channel 136 defined by threads between the exterior surface 118 of the processing tube 104 and an interior surface of the housing 106, this embodiment is not limiting. Similar thread-defined gas flow channels or similar attachment structures may be defined between adjacent surfaces of any one of the housing 106, processing tube 104, heat transfer casing 112 and/or chilled thermal mass element 114. Other structures not illustrated in the figures may be fabricated to serve the dual purpose of securely attaching various elements of the platelet lysis apparatus 102 to other elements, while also channeling or controlling the flow of expanding gas to provide for enhanced heat transfer.

Figure 9:
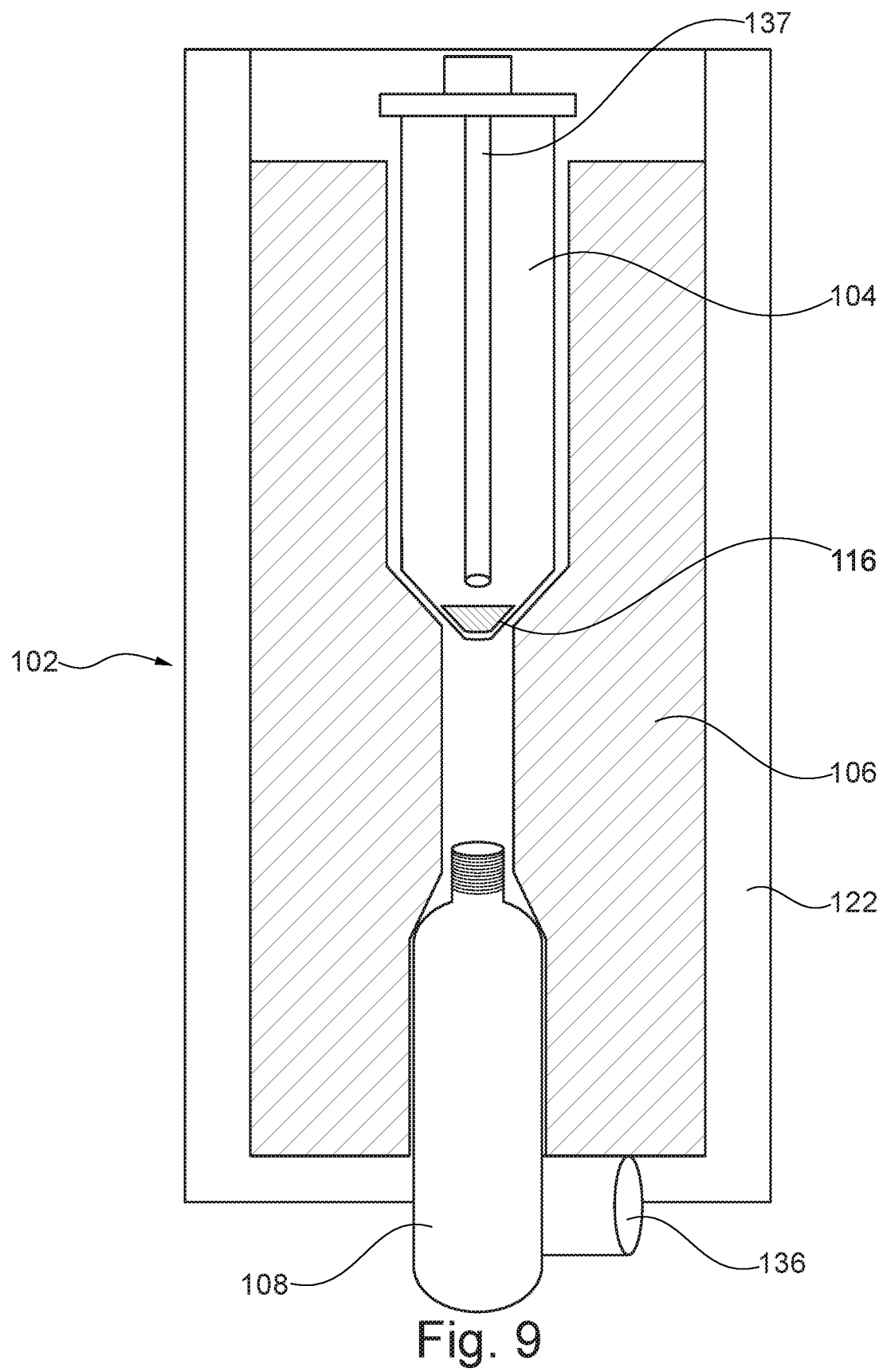
FIG. 9 is a schematic cross-sectional representation of another alternative platelet lysis apparatus embodiment.

The embodiments of FIGS. 1-8 are illustrated with a generic conical-bottom culture tube or centrifuge tube as the processing tube 104. In alternative embodiments, a customized processing tube 104 may be utilized. For example, the processing tube 104 of FIG. 6 includes a threaded portion for direct connection to a compressed gas source 108 and may include doubled exterior walls or other gas channeling structures. Further, the processing tube 104 of FIG. 6 may include a hollow needle or spike 107 positioned to pierce the metal seal 124 thereby releasing gas from the compressed gas source 108 as the compressed gas source 108 is threaded into full contact with the processing tube 104. The processing tube 104 embodiment of FIG. 9 includes a dedicated injection and/or extraction channel 137 incorporated into the cap 117 or septum, providing for simplified direct access to the platelet containing mixture or platelet pellet 116 within the processing tube 104. Other processing tubes may be fabricated from a material which facilitates heat transfer, including but not limited to stainless steel, another metal, or plastic with high thermal conductivity and the like.

Figure 10:
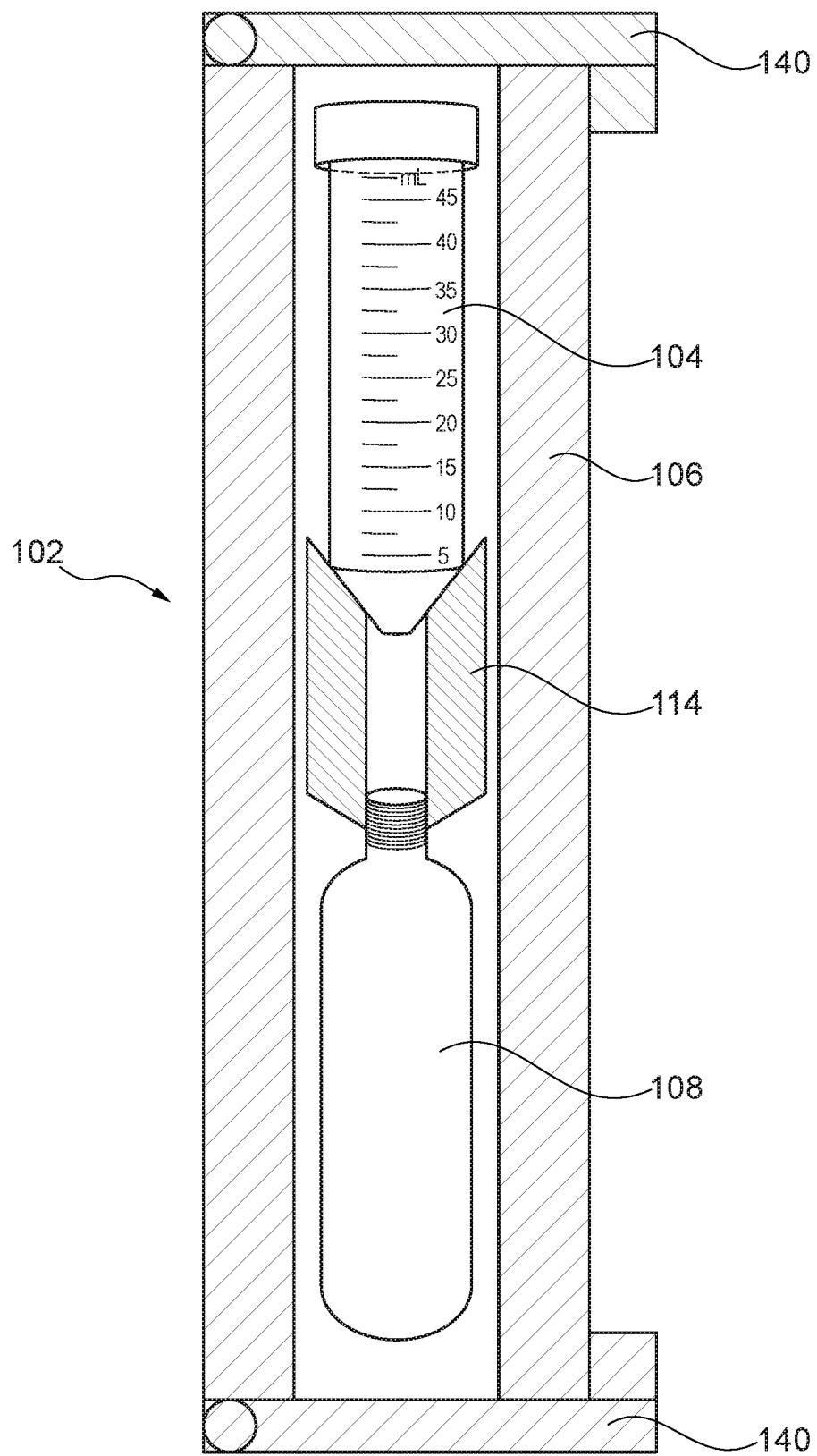
FIG. 10 is a schematic cross-sectional representation of another alternative platelet lysis apparatus embodiment.

As noted above, the housing 106 may include a secure lid 120 or other structure to prevent the release of compressed gas from forcibly expelling one or more components from the platelet lysis apparatus 102. Alternative embodiments of the housing 106 may include hinged lids 140 at one or both ends, as illustrated in FIG. 10, to secure the processing tube 104 and/or compressed gas source 108.

The embodiments of FIGS. 1-10 may be utilized as follows. Blood, bone marrow or another fluid can be drawn from a patient. This platelet containing fluid may be processed through one or more preliminary processing steps. For example, the platelet containing fluid may be processed in a centrifuge 105 to separate platelets from other whole blood components. Red blood cells, platelet poor plasma or other blood components may be withdrawn after initial processing leaving behind a platelet-rich mixture or platelet pellet. The platelet-rich mixture or platelet pellet may be extracted from an initial processing tube or more typically, subsequent processing steps may be carried out in the initial processing tube.

The platelets in processing tube 104 may be placed in any embodiment of platelet lysis apparatus 102 described herein or variations thereof. If the platelet lysis apparatus 102 includes a chilled thermal mass element 114 or chilled heat transfer casing 112, said element may be removed from a freezer 124 and attached to or placed within the housing 106 of the platelet lysis apparatus 102 prior to placement of the processing tube 104 within the platelet lysis apparatus 102. A source of compressed gas 108 is connected to the platelet lysis apparatus 102. Gas is released from the compressed gas source 108 and allowed to expand. The expanding gas is directly or indirectly contacted with an exterior surface 118 of the processing tube 104, causing heat exchange which freezes some or all of the platelets contained therein.

Subsequently, the processing tube 104 may be removed from the platelet lysis apparatus 102 and the frozen platelets thawed. The platelet thawing process may be accelerated in any manner, including but not limited to a warm liquid bath, placement of the processing tube 104 into a heater of any type or applying microwave energy to the processing tube 104.

Before and/or after freezing and/or thawing the platelets, an additional lysis-inducing agent, for example a salt solution or water may be added to the platelets in the processing tube 104. If necessary, the platelets may be subjected to more than one freeze and thaw cycle. Alternatively, the platelets may be subjected to one or more applications of ultrasonic energy, heat, mechanical vibration or the like to further promote lysis and activation.

After the lysed and/or activated platelets are thawed and any additional processing steps are performed, the lysed platelets may be suspended in an injectable fluid, for example water or autologous platelet poor plasma (PPP), and reinjected into a patient.

As noted above, all embodiments of a platelet lysis kit 100 will include a platelet lysis apparatus 102 as described herein. As illustrated in FIG. 1, kit embodiments may also include one or more syringes including but not limited to a syringe and needle 142 for adding a lysis agent, for example $CaCl_2$, to the platelets, a syringe and needle 144 for adding water to the platelets, a syringe and needle 146 for the extraction and/or addition of platelet poor plasma from and/or to the processing tube 104, or a syringe and needles 148 for re-injecting lysed and/or activated platelets back into the source patient. Kit embodiments may also include ancillary equipment, including but not limited to any desired number of processing tubes, tube racks, centrifuges, gloves, additional syringes and needles, septa, tube caps, refrigeration systems, chemical cooling packs, freezer systems, thawing systems, tubing, filters, other equipment and the like.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

What is claimed is:

1. A platelet lysis apparatus comprising:
   a sample tube;
   a compressed gas source;
   a housing supporting the sample tube and the compressed gas source;
   a conduit connected to the compressed gas source, said conduit extending from the compressed gas source to the sample tube; and
   a channel adjacent to the sample tube, said channel being defined by an interior surface of the housing and an exterior surface of the sample tube, wherein the conduit opens into the channel, and wherein the channel provides for the expansion of a gas from the compressed gas source into at least one of direct or indirect contact with an exterior surface of the sample tube, and wherein the direct or indirect contact between the expanding gas and the exterior surface of the sample tube reduces a temperature within the sample tube to freeze an unfrozen platelet containing mixture within the sample tube.

2. The platelet lysis apparatus of claim 1 further comprising a gas release mechanism providing for the selective release of gas from the compressed gas source.

3. The platelet lysis apparatus of claim 1 wherein the housing comprises an insulated exterior surface.

4. The platelet lysis apparatus of claim 1 further comprising a threaded connection between the sample tube and the housing, wherein said threaded connection comprises:
   one of a male or a female thread defined by an exterior surface of the sample tube; and
   a mating male or female thread defined by an interior surface of the housing, wherein a space between the male and female threads defines the channel between the exterior surface of the sample tube and the interior surface of the housing when the male and female threads are engaged.

5. The platelet lysis apparatus of claim 1 wherein the sample tube is provided with a metal exterior surface.

6. The platelet lysis apparatus of claim 1 further comprising a heat transfer casing in thermal contact with the sample tube, wherein the heat transfer casing is positioned to be in at least one of direct or indirect contact with the gas released from the compressed gas source.

7. The platelet lysis apparatus of claim 6, wherein the housing defines the channel from the conduit around an exterior surface of the heat transfer casing.

8. The platelet lysis apparatus of claim 7 further comprising a threaded connection between the heat transfer casing and the housing, wherein said threaded connection comprises:
   one of a male or a female thread defined by an exterior surface of the heat transfer casing; and
   a mating male or female thread defined by an interior surface of the housing, wherein a space between the male and female threads defines the channel between the exterior surface of the heat transfer casing and the interior surface of the housing when the male and female threads are engaged.

9. The platelet lysis apparatus of claim 6 wherein the heat transfer casing defines at least one opening through the heat transfer casing providing for direct contact between the expanding gas in the channel and the exterior surface of the sample tube.

10. The platelet lysis apparatus of claim 1 further comprising a thermal mass element in thermal contact with the sample tube.

11. The platelet lysis apparatus of claim 10 wherein the chilled thermal mass element comprises one of:
   a solid material defining an opening to receive the sample tube; and
   a liquid-filled container, said container defining an opening to receive the sample tube.

12. A method of causing platelet lysis comprising:
   providing a platelet lysis apparatus comprising:
   a sample tube;
   a compressed gas source;

a housing supporting the sample tube and the compressed gas source;

a conduit connected to the compressed gas source, said conduit extending from the compressed gas source to the sample tube; and a channel adjacent to the sample tube, said channel being defined by an interior surface of the housing and an exterior surface of the sample tube, wherein the conduit opens into the channel, and wherein the channel provides for the expansion of a gas from the compressed gas source into at least one of direct or indirect contact with an exterior surface of the sample tube;

releasing the gas from the compressed gas source into the conduit;

flowing the gas from the conduit to the channel; and expanding the gas in the channel as the gas is in at least one of direct or indirect contact with an exterior surface of the sample tube, wherein the direct or indirect contact between the expanding gas and the exterior surface of the sample tube reduces a temperature within the sample tube to freeze an unfrozen platelet containing mixture within the sample tube.

13. The method of claim 12 further comprising:

providing a gas release mechanism in fluid communication with the compressed gas source; and selectively releasing gas from the compressed gas source using the gas release mechanism.

14. The method of claim 12 further comprising:

providing a threaded connection between the sample tube and the housing, wherein said threaded connection comprises:

one of a male or a female thread defined by an exterior surface of the sample tube; and a mating male or female thread defined by an interior surface of the housing, wherein a space between the male and female threads defines the channel between the exterior surface of the sample tube and the interior surface of the housing when the male and female threads are engaged.

15. The method of claim 12 further comprising providing a heat transfer casing in thermal contact with the sample tube, wherein the heat transfer casing is positioned to be in at least one of direct or indirect contact with the expanding gas in the channel.

16. The method of claim 15 further comprising:

providing a threaded connection between the heat transfer casing and the housing, wherein said threaded connection comprises:

one of a male or a female thread defined by an exterior surface of the heat transfer casing; and a mating male or female thread defined by an interior surface of the housing, wherein a space between the male and female threads defines the channel between the exterior surface of the heat transfer casing and the interior surface of the housing when the male and female threads are engaged.

17. The method of claim 12 further comprising:

providing a chilled thermal mass element;

chilling the thermal mass element; and placing the thermal mass element into thermal contact with the sample tube.

* * * * *